(12) United States Patent
Miyata

(10) Patent No.: US 7,029,906 B2
(45) Date of Patent: Apr. 18, 2006

(54) CARBONYL STRESS-AMELIORATING AGENTS

(75) Inventor: Toshio Miyata, 102, Ekuseru Isehara, 16-25, Sakuradai 2-chome, Isehara-shi, Kanagawa 259-1132 (JP)

(73) Assignees: Toshio Miyata, Kanagawa (JP); Kiyoshi Kurokawa, Tokyo (JP); Tokai University Education System, Tokyo (JP)

( * ) Notice: Subject to any disclaimer, the term of this patent is extended or adjusted under 35 U.S.C. 154(b) by 15 days.

(21) Appl. No.: 10/168,695

(22) PCT Filed: Dec. 15, 2000

(86) PCT No.: PCT/JP00/08911

§ 371 (c)(1),
(2), (4) Date: Dec. 10, 2002

(87) PCT Pub. No.: WO01/45733

PCT Pub. Date: Jun. 28, 2001

(65) Prior Publication Data

US 2003/0143215 A1    Jul. 31, 2003

(30) Foreign Application Priority Data

Dec. 20, 1999  (JP) .................................. 11-360479

(51) Int. Cl.
C07K 1/00 (2006.01)
A61K 38/00 (2006.01)
B01D 61/26 (2006.01)
C12N 9/88 (2006.01)

(52) U.S. Cl. ...................... 435/269; 435/232; 210/646; 514/18

(58) Field of Classification Search ................. 514/18; 435/232, 269; 210/633, 646, 679
See application file for complete search history.

(56) References Cited

U.S. PATENT DOCUMENTS 4,356,267 A * 10/1982 Callegaro et al. ........... 435/179
6,448,062 B1 * 9/2002 Huth et al. .................. 435/264

FOREIGN PATENT DOCUMENTS

| EP | 277754 A1 * | 8/1988 |
| JP | 5-105633 | 4/1993 |
| WO | WO 00/10606 | 3/2000 |
| WO | WO 00/69466 | 11/2000 |

OTHER PUBLICATIONS

Piskorska et al. "Synthesis of S-lactoyl-glutathione using glyoxalase 1 bound to sepharaose 4B" Experientia (1976) 32(11): 1382-3.*
Miura et al. "Detoxificatioon of ammonia by immoblized urea cycle enzymes" Artificial Organs (1981) 5(1): 72-79.*
Patterson et al. "enzymatic conversion of alpha-keto aldehydes to optically active alpha-hydrozy acids glyoxalase I and II" J. Org. Chem. (1981) 46: 4682-85.*
Shinohara et al. Overexpression of glyoxalase I in bovine endothelial cells intracellular advanced glycation endproduct formation and prevents hyperglycemia-induced increases in macromolecular endocytosis J. Clin. Invest. (1998) 111(5): 1142-7.*
Miyata et al.. "Alterations in nonenzymic biochemistry in uremia: Origin and significance of 'carbonyl stress' in long-term uremic complications" Kidney International (Feb. 1999) 55: 389-399.*
Britz, M. "Selecting host-vector systems for productionof cloned proteins" Australian J. Biotechnol. (1987) 1(3): 29-34 and 36-37.*
Inoue et al. "Identification of the structural gene for glyoxalase I from *Saccharomyces cerevisiae*" J. Biol. Chem. (1996) 271(42): 25958-65.*
Abordo EA et al., Biochem Pharmacol, 58(4), 641-9 (1999).
Thornalley PJ, Endocrinology and Metabolism, 3(3), 149-66 (1996).
Ruggiero-Lopez D, et al, Biochem Pharmacol, 58(11), 1765-73 (1999).
International Search Report, Mar. 6, 2001.

* cited by examiner

Primary Examiner—Jean C. Witz
Assistant Examiner—Susan Hanley
(74) Attorney, Agent, or Firm—Ingrid A. Beattie; Cynthia A. Kozakiewicz; Mintz Levin

(57) ABSTRACT

Carbonyl stress-ameliorating agents have been provided, which contain an enzyme having a glyoxalase I activity and a carbonyl compound-reducing agent as the active ingredients. The carbonyl stress-ameliorating agents of the present invention rapidly eliminate carbonyl compounds, and thus ameliorate carbonyl induced stress conditions.

7 Claims, 6 Drawing Sheets

CARBONYL STRESS-AMELIORATING AGENTS

TECHNICAL FIELD

The present invention relates to carbonyl stress-ameliorating agents.

BACKGROUND ART

An enhanced state of protein modification due to increased in vivo production of various sugar-derived or lipid-derived carbonyl compounds via non-enzymatic biochemical reactions is called "carbonyl stress" (Miyata et al. Kidney Int. 55: 389–399, 1999; Miyata et al. J. Am. Soc. Nephrol., 11:1744–1752,2000). These carbonyl compounds have been reported to be involved in adult diseases, such as diabetes mellitus and arteriosclerosis, as well as aging, via Maillard reaction. The Maillard reaction is a non-enzymatic glycation reaction between a reducing sugar, such as glucose, and amino acids or proteins. Maillard reported this reaction in 1912, focusing on a phenomenon of brown coloration arising upon heating a mixture consisting of amino acid and reducing sugar (Maillard, L. C., Compt. Rend. Soc. Biol., 72: 599, 1912). The Maillard reaction is involved in brown coloration, generation of aromatic components, taste, protein denaturation, and such reactions during heating or storage of foods. Therefore, this reaction has been mainly studied in the field of food chemistry.

However, in 1968, glycated hemoglobin (HbAlc), a micro fraction of hemoglobin, was identified in vivo and shown to increase in diabetic patients (Rahbar. S., Clin. Chim. Acta, 22: 296, 1968). These findings brought attention to the significance of in vivo Maillard reactions and the relationship between the reaction, the onset of adult diseases (such as diabetic complications and arteriosclerosis) and in progress of aging. For example, pyrraline and pentosidine, which are the late-stage products formed at post-Amadori compound formation reaction stages (advanced glycation end products; hereinafter abbreviated as AGE), are considered to serve as indices of aging and diabetes mellitus. In fact, highly reactive carbonyl compounds and AGE are accumulated at very high levels in the blood and tissues of chronic renal failure patients, regardless of the presence or absence of hyperglycemia (Miyata, T. et al., Kidney Int., 51: 1170–1181, 1997; Miyata, T. et al., J. Am. Soc. Nephrol., 7: 1198–1206, 1996; Miyata, T. et al., Kidney Int. 55: 389–399, 1999; Miyata, T. et al., J. Am. Soc. Nephrol. 9: 2349–2356, 1998). This accumulation is ascribed to as carbonyl stress in renal failure, where proteins are modified as a result of the Maillard reaction when carbonyl compounds derived from sugars and lipids react with amino groups (Miyata, T. et al., Kidney Int. 55: 389–399, 1999). Recently, the involvement of carbonyl stress in the onset and progress of dialysis amyloidosis and arteriosclerosis, which are complications of renal failure, has been reported (Miyata et al. J. Clin. Invest., 92: 1243–1252, 1993; Miyata et al. Proc. Natl. Acad. Sci. USA, 93, 2353–2358, 1996; Miyata et al. FEBS Lett., 437, 24–28, 1998; Miyata et al. FEBS Lett., 445, 202–206, 1999). Hence, the pathophysiological significance of carbonyl stress in renal failure is established.

Therefore, improving the carbonyl stress state via removal of in vivo-generated carbonyl compounds can result in the suppression of AGE formation that is associated with renal failure, reducing tissue damage and complications.

Furthermore, during peritoneal dialysis waste products are excreted from the blood across the peritoneum to the peritoneal dialysate. In blood of renal-failure patients, peritoneal dialysate with high osmotic pressure (dialysate containing glucose, icodextrin; amino acids, etc.) accumulate highly reactive carbonyl compounds via peritoneum into the peritoneal dialysate in peritoneal cavity. This results in an increase in the carbonyl compound concentration within the peritoneal dialysate, thereby causing a carbonyl stress state. As a result, the peritoneal function is lowered, due to the modification of intraperitoneal proteins with carbonyl; this reaction, in turn is presumed to be involved in the impairment of water-removing ability and ingravescence of peritoneal sclerosis (Miyata, T. et al., Kidney Int., 58:425–435, 2000; Inagi R., et al., FEBS Lett., 463:260–264, 1999; Ueda, Y., et al., Kidney Int. (in press); Combet, S., et al., J. Am. Soc. Nephrol., 11:717–728, 2000).

Indeed, immunohistochemical examinations of the endothelia and mesothelia have demonstrated that the intraperitoneal carbonyl stress state in peritoneal dialysis patients is induced by glucose contained in the peritoneal dialysate (Yamada, K. et al., Clin. Nephrol., 42: 354–361, 1994; Nakayama, M. et al., Kidney Int., 51: 182–186, 1997; Miyata, T. et al., Kidney Int., 58: 425–435, 2000; Inagi R., et al., FEBS Lett., 463: 260–264, 1999; Combet, S., et al., J. Am. Soc. Nephrol., 11: 717–728, 2000). Furthermore, the methylglyoxal contained in the peritoneal dialysate has been revealed to act on endothelial and mesothelial cells to enhance the production of vascular endothelial growth factor (VEGF), an agent presumed to play a central role in the impairment of peritoneal function (Combet et al. J. Am. Soc. Nephrol., 11: 717–728, 2000; Inagi et al. FEBS Let, 463: 260–264, 1999). Hence, carbonyl stress is also presumed to cause morphological changes in the peritoneum accompanied by functional (water-removing ability) impairment in dialysis patients. Therefore, a method to ameliorate the stress is required in the art.

Recently, the mechanism of the in vivo system to eliminate and metabolize carbonyl compounds has been revealed. A number of enzymes and enzyme pathways, such as aldose reductase, aldehyde dehydrogenase, and glyoxalase, have been reported to be involved in the elimination of carbonyl compounds. The decrease in the activities of these carbonyl compound-eliminating systems leads directly to a rise in the levels of many types of carbonyl compounds. Redox coenzymes, such as glutathione (GSH) and NAD(P)H, play important roles in such pathways (Thornalley P. J., Endocrinol Metab 3: 149–166, 1996). Carbonyl compounds, such as methylglyoxal and glyoxal, react non-enzymatically with thiol group of GSH and are eventually metabolized by glyoxalase. NAD(P)H activates glutathione reductase to increase the GSH level. Therefore, decrease of GSH and NAD(P)H by an imbalance in intracellular redox mechanisms blocks the carbonyl compound-elimination system and leads to the accumulation of AGE. In fact, blood GSH levels in patients with diabetes mellitus is reported to be reduced, whereas the levels of the carbonyl compound, methylglyoxal, in these patients are reported to be elevated.

As described above, a decrease in concentration of redox coenzymes, such as GSH and NAD(P), is suspected to be the cause of AGE formation because of a decreased elimination of carbonyl compounds. Thus, carbonyl stress was suggested to be relieved by elevating thiol level. Based on this theory, the present inventors tried to directly administer thiol compounds, such as GSH and cystein. In fact, incubation of sera from a normal person and patients with diabetes mellitus by adding these thiol compounds suppressed the production of AGE. However, a long period was required to gain such suppression, making this impractical.

Furthermore, AGE has been known to be generated through a carbonyl-amino chemical reaction between carbonyl compounds and proteins. Hence, it was concluded that carbonyl stress can be relieved with compounds that can chemically trap these products. Such compounds include hydrazine group-containing aminoguanidine (Brownlee M. et al., Science 232: 1629–1632, 1986), and 2-isopropylidenehydrazono-4-oxo-thiazolidin-5-ylacetanilide (Nakamura S. et al., Diabetes 46: 895–899, 1997). Beside these compounds, biguanides, such as metformin and buformin, can also trap carbonyl compounds. In vitro experiments demonstrated that all of these compounds efficiently trap carbonyl compounds, methylglyoxal and glyoxal (Miyata T., J. Am. Soc. Nephrol. 11: 1719–1725, 2000). However, in spite of the efficient inhibition of the production of AGE by these compounds, the specificity of these compounds to carbonyl compounds is low since they react with all types of carbonyl compounds. As a result, these compounds not only trap sugar-derived or lipid-derived carbonyl compounds that are deleterious to living cells, but they also trap carbonyl groups, such as pyridoxal, which are essential for living cells.

To solve the above problem, development of carbonyl stress-ameliorating agents, which can rapidly ameliorate carbonyl stress and are specific to sugar or lipid-derived deleterious carbonyl compounds, is desired in the art.

An in vivo system is known wherein one of deleterious carbonyl compounds, methylglyoxal, is converted to lactic acid. Methylglyoxal is converted to lactic acid in the glyoxal system that consists of GSH, glyoxal I, and glyoxal II. The glyoxalase I has also been known to act on other ketoaldehyde compounds besides methylglyoxal. However, the physiological role of this system remains to be understood. Furthermore, the use of this system for ameliorating carbonyl stress state in living cells has not been previously reported.

DISCLOSURE OF THE INVENTION

The object of the present invention is to provide carbonyl stress-ameliorating agents that can rapidly eliminate carbonyl compounds.

The present inventor extensively studied to develop an effective method for eliminating and detoxifying carbonyl compounds in solutions, and focused on a detoxification system for carbonyl compounds called "glyoxalase system." The glyoxalase system, is a detoxification reaction system composed of two enzymes, glyoxalase I (lactoyl GSH lyase) and glyoxalase II (hydroxy acyl GSH hydrase). The carbonyl compound, methylglyoxal, has been known to be converted to lactic acid in the presence of GSH through the detoxification reaction.

The present inventor discovered that methylglyoxal can be rapidly eliminated by additionally introducing glyoxalase I to the reaction solution of the methylglyoxal-trapping reaction with glutathione. Finally, the present inventor proved that in the presence of both glutathione and glyoxalase I other carbonyl compounds as well as methylglyoxal in the peritoneal dialysate were rapidly eliminated.

More specifically, the present invention relates to carbonyl stress-ameliorating agents and peritoneal dialysates using the agents as follows:

(1) a carbonyl stress-ameliorating agent comprising, as active ingredients, an enzyme having glyoxalase I activity and a carbonyl compound-reducing agent;

(2) the carbonyl stress-ameliorating agent of (1), which additionally contains an enzyme having glyoxalase II activity as an active ingredient;

(3) the carbonyl stress-ameliorating agent of (1), wherein the carbonyl compound-reducing agent is reduced glutathione and/or derivative thereof;

(4) the carbonyl stress-ameliorating agent of (3), wherein the final concentration of the reduced glutathione in a medium for eliminating carbonyl compounds is 0.1 to 50 mM;

(5) the carbonyl stress-ameliorating agent of (1), wherein the amelioration of carbonyl stress is achieved by eliminating 2-oxoaldehyde;

(6) the carbonyl stress-ameliorating agent of (5), wherein the 2-oxoaldehyde is a compound selected from the group consisting of glyoxal, methylglyoxal, and 3-deoxyglucosone;

(7) the carbonyl stress-ameliorating agent of (1), wherein the enzyme having glyoxalase I activity is immobilized on a carrier;

(8) a method for eliminating carbonyl compounds, which comprises the step of contacting the carrier of (7) with patient's blood or peritoneal dialysate in the presence of a carbonyl compound-reducing agent;

(9) a peritoneal dialysate containing the carbonyl stress-ameliorating agent of (1); and

(10) a method for ameliorating carbonyl stress in peritoneal dialysate, which comprises the step of contacting the peritoneal dialysate with an enzyme having glyoxalase I activity in the presence of a carbonyl compound-reducing agent.

Further, the present invention relates to the use of enzymes having the glyoxalase I activity and carbonyl compound-reducing agents to produce the carbonyl stress-ameliorating agents. The present invention also relates to the use of carriers, on which an enzyme having the glyoxalase I activity has been immobilized, to produce carbonyl-compound adsorbents.

A carbonyl stress-ameliorating agent of the present invention contains, as active ingredients, an enzyme having glyoxalase I activity and a carbonyl compound-reducing agent. As used herein, the term "amelioration of carbonyl stress" refers to eliminating carbonyl compounds in a medium which is contacted with living bodies, and thus, alleviating protein modification. "Elimination of carbonyl compounds" indicates irreversible elimination of the reactivity of carbonyl groups. The term "medium contacted with living body" specifically refers to peritoneal dialysate (hereinafter abbreviated as "CAPD solution"), blood, and other body fluids.

The phrase "a carbonyl compound-reducing agent that can be used in the present invention" refers to a compound that reduces carbonyl compound to a compound that serves as a substrate for enzymes having glyoxalase I activity. Arbitrary compounds can be used as the carbonyl compound-reducing agent of the invention so long as they fulfill the above requirement. Such compounds include, for example, reduced glutathione (GSH) and derivatives thereof. These compounds may be pharmacologically acceptable salts. For example, reduced GSH binds to methylglyoxal, a carbonyl compound, to produce hemithioacetal. This reaction is a non-enzymatic reaction. The hemithioacetal thus produced serves as a substrate for enzymes having glyoxalase I activity. Further, any glutathione derivative can be used according to the present invention so long as it produces a carbonyl compound, which serves as a substrate for enzymes having glyoxalase I activity. More preferably, the glutathione derivatives are those, which have thiol groups reacting with carbonyl compounds to produce thiolester compounds. Specifically, such glutathione derivatives include, for example, acetylglutathione, aspartathion, isoglutathione, etc.

A carbonyl compound-reducing agent should be used at a concentration that ensures the elimination of carbonyl compounds in the reaction. Specifically, for example, when GSH is used to eliminate carbonyl compounds in CAPD solution, the GSH can be used at a final concentration of 0.1 to 50 mM, more preferably 1 to 10 mM, in the medium (herein, the CAPD solution) from which the carbonyl compounds are to be eliminated. With a concentration of GSH within this range, carbonyl compounds in a typical CAPD solution can be converted nearly completely and rapidly to substrates for enzymes having glyoxalase I activity. However, it is difficult to predict the quantity of carbonyl compounds in a CAPD solution during dialysis. Thus, when an enhanced carbonyl stress state is suspected in patient, GSH can be used at a higher ensuring concentration.

According to the present invention, the term "enzymes having glyoxalase I activity" refers to enzymes having a catalytic activity functionally equivalent to that of glyoxalase I. Glyoxalase I is also called lactoyl GSH lyase (EC. 4.4.1.5), which uses, as substrate, compounds wherein a carbonyl compound-reducing agent, such as reduced glutathione, is linked to the aldehyde group of keto-aldehyde (2-oxoaldehyde) compound. A representative substrate compound for glyoxalase I is, for example, hemimercaptal (hemithioacetal), which consists of methylglyoxal linked to reduced glutathione. Enzymes having glyoxalase I activity catalyze such reactions wherein such substrate compounds are converted to thiolester compounds. Any enzymes and reducing agents can be used in the present invention, so long as they can convert the aldehyde group of a keto-aldehyde compound to a thiolester in the presence of a carbonyl compound-reducing agent. The scheme of the enzyme reaction is as follows:

The reaction formula indicates that hemithioacetal, which is produced through the binding of a carbonyl compound, methylglyoxal, with GSH, is converted and detoxified to S-lactoyl glutathione by an enzyme having glyoxalase I activity. This reaction is an irreversible reaction. Thus, the nontoxic S-lactoyl glutathione is stable and a reverse reaction producing methylglyoxal substantially does not proceed.

The present inventor discovered that a wide variety of substances, including methylglyoxalase which produce carbonyl stress state in vivo, can be rapidly eliminated via the combined use of GSH and enzyme having glyoxalase I activity, thereby supporting the effectiveness of the combination as an carbonyl stress-ameliorating agent.

Enzymes known to possess glyoxalase I activity are derived from various sources as follows:

mammalian tissues (Methods Enzymol. 90, 536–541, 1982; Methods Enzymol. 90, 542–546, 1982); yeast (FEBS Lett. 85, 275–276, 1978;

Biochem. J. 183, 23–30, 1979);

bacteria (Biochem. Biophys. Res. Commun., 141, 993–999, 1986); and human (J. Biol. chem. 268, 11217–11221, 1993).

Among these enzymes, human glyoxalase I are expected to be safe when administered to human patients. Methods for purifying the glyoxalase I enzymes are well known in the art. An enzyme having glyoxalase I activity used in the present invention may be a native enzyme or a genetic recombinant. For example, the structure of the human glyoxalase I gene has been elucidated (J. Biol. chem. 268, 11217–11221, 1993). Therefore, a recombinant protein thereof can be readily obtained using this known gene. Furthermore, the enzymes having glyoxalase I activity of the present invention can be (other than those enzymes having the same amino acid sequence as the native enzyme) those where mutations are introduced to improve their stability, activity, etc. Methods for artificially introducing mutations into amino acid sequences are known in the art. For example, codons in nucleotide sequences can be partially modified according to site-specific mutagenesis (Mark, D. F. et al. Proc. Natl. Acad. Sci. U.S.A. 81,5662 (1984)) using synthetic oligonucleotide primers that encode the desired mutated amino acids.

Besides mutating its amino acid sequence, an enzyme having glyoxalase I activity of the present invention may be chemically modified. For example, binding to polyethylene glycol has been known to improve enzyme stability in some cases. Alternatively, a method of immobilizing enzyme proteins on solid-phase carriers is also commonly used for the convenience of enzyme protein recovery. Such chemical modification methods can be applied to enzymes having glyoxalase I activity according to the present invention.

An enzyme having glyoxalase I activity is used at a concentration that ensures rapid elimination of substrate compounds produced through the reaction between carbonyl compounds and carbonyl compound-reducing agents. For example, when carbonyl compounds are eliminated from CAPD. solution, the rapid elimination of carbonyl compound can be achieved by 10 to $10^4$ U glyoxalase I, preferably 10 to $10^3$ U glyoxalase I, per 1 L of CAPD solution. 1 U of glyoxalase I is defined as a quantity of enzyme required for producing 1 µmol S-lactoyl glutathione from methylglyoxal and reduced glutathione in 1 minute.

Enzymes having glyoxalase II activity can also be formulated into a carbonyl stress-ameliorating agent of the present invention. Glyoxalase II is a hydrolytic enzyme, which is also called hydroxy acyl GSH hydrase (EC.3.1.2.6). In vivo, this enzyme catalysis the hydrolysis of S-D-lactoyl glutathione, (which is produced by the action of glyoxalase I) to produce lactic acid and the regeneration of reduced glutathione. The glyoxalase system composed of glyoxalase I, glutathione (GSH), and glyoxalase II is described below.

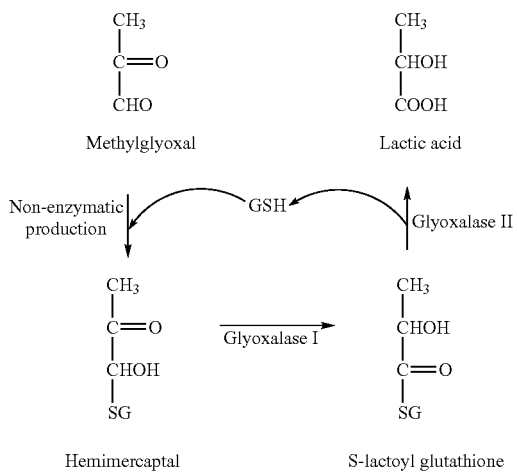

Glyoxalase II enzymes including the human-derived enzyme (J. Biol. Chem. 271, 319–323, 1996) has also been isolated. Any of the known glyoxalase II enzymes can be used in the present invention. Like enzymes having glyoxalase I activity, native form or genetic recombinant enzymes having glyoxalase II activity can be used in the present invention. Further, enzymes comprising mutations in the amino acid sequence can also be utilized in the present invention.

When an enzyme having glyoxalase II activity is used in combination with a carbonyl stress-ameliorating agent of the present invention, the two can be formulated by combining them prior to use or contacting them at the time of use. Further, when enzymes having glyoxalase I activity are used as immobilized enzymes, the enzyme having glyoxalase II activity can also be used in an immobilized form. The immobilization of enzymes can be achieved by either of the two methods: (1) the enzymes may be mixed and then immobilized together; or (2) the enzymes are separately immobilized and then are combined together. The enzymes having glyoxalase II activity are preferably used at a concentration ensuring rapid elimination of the reaction products of an enzyme having glyoxalase I activity. Specifically, when 1U of glyoxalase I is used, the amount of the enzymes having glyoxalase II activity is preferably 0.5 to 10 U, more preferably 1 to 5 U. 1 U of glyoxalase II is defined as a quantity of the enzymes required for the production of 1 µmol lactic acid from S-D-lactoyl glutathione in 1 minute.

According to the present invention, carbonyl compounds containing oxoaldehyde (R—CO—CHO) as a fundamental structure that generates carbonyl stress in living bodies are to be eliminated. Such compounds include, for example, compounds, which accumulate in blood of renal failure patients in response to oxidative stress, as follows:
Carbonyl compounds derived from carbohydrates:
glyoxal
methylglyoxal
3-deoxyglucosone.

A carbonyl stress-ameliorating agent of the present invention can be applied to living bodies affected with carbonyl stress. Specifically, for example, the agent can be administered parenterally, or into the circuit of hemodialysis or peritoneal dialysis. Alternatively, a carbonyl stress-ameliorating agent of the present invention may be added prior to CAPD solution. In this case, a carbonyl stress-ameliorating agent of the present invention should be aseptically added to the heat-sterilized CAPD solution. Alternatively, a carbonyl stress-ameliorating agent of the present invention can also be added at the time of use.

A carbonyl stress-ameliorating agent can be added aseptically by aseptically filling a conventional multi-compartment container or pre-filled syringe with the carbonyl stress-ameliorating agent and mixing at the time of use. Exemplary multi-compartment containers are: fractionated-bag container wherein the compartments can be connected; kit containers comprising communicating means, such as double-ended needle; and so on. One compartment of a multi-compartment container is filled with peritoneal dialysate while the other compartment is filled with a carbonyl stress-ameliorating agent of the present invention. The compartments are connected at the time of use.

To ameliorate carbonyl-stress state, a method that comprises a step of contacting CAPD solution is also effective. Herein, the CAPD solution contains immobilized enzyme (having glyoxalase I activity of the present invention) and a carbonyl compound-reducing agent, such as reduced GSH; and hereinafter, unless otherwise specified, the term "CAPD solution" refers to a solution comprising a carbonyl compound-reducing agent. For example, carbonyl compounds that are produced and accumulated during storage in CAPD solution for peritoneal dialysis can be eliminated by placing the solution in a container wherein enzymes having glyoxalase I activity are immobilized on the inner surface or in a container containing enzymes having glyoxalase I activity immobilized on carriers, such as bead or fiber. In the later case, the insoluble carriers can be removed from the peritoneal dialysate by filtration.

A cartridge for eliminating carbonyl compounds can be prepared by filling a column with bead-shaped or fibrous carriers, on which the enzyme having glyoxalase I activity has been immobilized. The CAPD solution can be introduced into the peritoneal cavity after contacting the solution with this cartridge. The carbonyl compound-reducing agent required for eliminating carbonyl compounds may be added prior to the CAPD solution. In cases where the cartridge for eliminating carbonyl compounds is contacted at the time of introduction to the peritoneal cavity, carbonyl compounds derived from the patient that accumulated during dialysis cannot be removed but those existing in the dialysate can be removed. Alternatively, when peritoneal dialysis is conducted by circulating peritoneal dialysate in a closed circuit with a small circulating pump, carbonyl compounds that accumulate in peritoneal cavity during dialysis can be removed, as well as those in the peritoneal dialysate by placing the above-mentioned cartridge for eliminating carbonyl compounds, which contains the immobilized carbonyl stress-ameliorating agent, in the circuit.

When combining an enzyme having glyoxalase II activity into a carbonyl stress-ameliorating agent of the present invention, it can be previously formulated with an enzyme having glyoxalase I activity. Alternatively, when an immobilized enzyme is used as the enzyme having glyoxalase I activity, the enzyme having glyoxalase II activity can also be used in an immobilized form. Specifically, a mixed column containing both enzymes having the glyoxalase I activity and glyoxalase II activity may be used, or the enzyme having glyoxalase II activity can be placed downstream to the enzyme having glyoxalase I activity. Alternatively, the elimination of carbonyl compounds can be achieved by a system wherein either one of the enzymes is immobilized while the other is in a free state.

The method for removing carbonyl compounds according to the present invention is applicable to methods for ameliorating carbonyl stress, which comprises contacting with blood, dialysate, and such outside living bodies. Enzymes having glyoxalase I activity are advantageously immobilized for such methods.

According to the present invention, there is no particular limitation on the carrier that is used for immobilizing an enzyme having glyoxalase I activity of the present invention, as long as the carrier is harmless to humans and is sufficiently safe and stable as to be in direct contact with blood or dialysate. Such materials include, for example, synthetic or natural organic macro-molecular compounds; inorganic materials, such as glass bead, silica gel, alumina, and active charcoal; and materials coated with polysaccharide(s), synthetic polymer(s), etc.; and so on.

A carrier consisting of macromolecular compounds include, for example, polymethyl methacrylate polymer, polyacrylonitrile polymer, polysulfone polymer, vinyl polymer, polyolefin polymer, fluorine polymer, polyester polymer, polyamide polymer, polyimide polymer, polyurethane polymer, polyacrylic polymer, polystyrene polymer, polyketone polymer, silicon polymer, cellulose polymer, chitosan polymer, etc. More specifically, carriers are exemplified by polysaccharides, such as agarose, cellulose, chitin, chitosan, sepharose, dextran, etc., and derivatives thereof; polyester, polyvinyl chloride, polystyrene, polysulfone, polyether sulfone, polypropylene, polyvinyl alcohol, polyallylehter sulfone, polyacrylic acid ester, polymethacrylic acid ester, polycarbonate, acetylated cellulose, polyacrylonitrile, polyethylene terephthalate, polyamide, silicon resin, fluororesin, polyurethane, polyether urethane, polyacrylamide, and derivatives thereof; and so on. The macromolecular materials can be used alone or in combination of two or more kinds of macromolecules. In the latter case, an enzyme having glyoxalase I activity of the present invention is immobilized on at least one of the macromolecules. Also, an enzyme having glyoxalase I activity may be immobilized alone on a carrier, or in combination with an enzyme having glyoxalase II activity on the carrier.

According to the present invention, there is no limitation on the shape of carrier. For example, the carrier can be membranous, fibrous, granular-shaped, hollow fiber-like, non-woven fabric-like, porous, honeycomb-shaped, and so on. The area of the carrier, to be contacted with blood or peritoneal dialysate, can be controlled by changing the thickness, surface area, diameter, length, shape, and/or size of the carrier.

An enzyme having glyoxalase I activity of the present invention can be immobilized on the above-mentioned carrier using well known methods, such as physical adsorption, a specific biochemical binding reaction, ion binding, covalent bonding, grafting, etc. According to the specific utility desired, spacers can be inserted between carrier and enzyme having glyoxalase I activity. Preferably, a carrier and an enzyme having glyoxalase I activity are bound by covalent bonds so as to minimize the amount of enzyme released. Functional groups on the carrier are utilized for covalently binding an enzyme having glyoxalase I activity thereto. The functional groups include, for example, hydroxyl group, amino group, aldehyde group, carboxyl group, thiol group, silanol group, amide group, epoxy group, succinylimide group, etc. However, the functional groups of the present invention are not limited to these groups. The covalent bonds are exemplified by ester linkage, ether linkage, amino linkage, amid linkage, sulfide linkage, imino linkage, disulfide linkage, and so on.

The carrier with an enzyme having glyoxalase I activity of the present invention immobilized on it can be sterilized via conventional sterilization methods. Specifically, sterilization methods include gamma-ray irradiation, gas sterilization, and so on.

Carriers immobilized with an enzyme having glyoxalase I activity of the present invention can be contacted with blood in various ways. Examples thereof include: a method of eliminating carbonyl compounds in patient blood by infusing the blood collected from the patient into a blood bag filled with carriers, on which an enzyme having glyoxalase I activity has been immobilized; a method where blood is circulated in a cartridge column filled with bead carriers or fiber carriers, or the like, on which an enzyme having glyoxalase I activity has been immobilized. Instead of whole blood, blood plasma may also be treated according to the method. The treated blood may be returned to the patient or, if required, may be stored in a blood bag or the like. Carbonyl compounds that generate and/or accumulate during storage can also be eliminated by adding carriers immobilized with enzymes having glyoxalase I activity into the blood bags.

The contact between blood, carbonyl compound-reducing agents, and carriers, on which an enzyme having glyoxalase I activity of the present invention has been immobilized, can be carried out during the blood purification step, including hemodialysis, blood filtration, blood filtration dialysis, blood adsorption and blood plasma separation.

For example, both hemodialysis and elimination of carbonyl compounds can be carried out simultaneously in hemodialysis patients by placing carriers on which an enzyme having glyoxalase I activity of the present invention has been immobilized in the hemodialysis circuit, and conduct dialysis in the presence of carbonyl compound-reducing agents. Herein, an enzyme having glyoxalase I activity of the present invention is preferably immobilized on the hemodialysis membrane. Known types of dialysis membranes can be used as carriers. Examples include: cellulose derivatives, such as regenerated cellulose, and cellulose triacetate; polymethyl methacrylate; polyolefin; polysulfone; polyacrylonitrile (PAN); polyamide; polyimide; polyether nylon; silicon; polyester copolymers; and so on; however, the present invention is not limited thereto. Instead of using a dialysis membrane as a carrier, a column filled with carriers, on which an enzyme having glyoxalase I activity of the present invention has been immobilized, may indeed be placed in the hemodialysis circuit as described above. By contacting patient's blood, in the presence of carbonyl compound-reducing agents, with carriers on which the enzyme having glyoxalase I activity has been immobilized, carbonyl compounds are trapped from the blood, and the damaging activity of the compounds against living body is eliminated and rendered nontoxic. Anticoagulants may be combined to prevent blood-clotting during extra corporeal circulation. Such anticoagulants include, for example, heparin, low-molecular-weight heparin, Futhan (Nafamostat mesilate), and so on. They may also be immobilized on carriers.

It is possible that there may be-some cases where carbonyl compounds in patient's blood are not completely eliminated during dialysis if the quantity of carbonyl-stress ameliorating agent of the present invention used for the contact with blood or dialysate is too small. Pre-determination of the quantity of carbonyl compounds in the patient's blood is particularly difficult. Thus, to be most effective, it is advantageous to maintain as many carbonyl stress-ameliorating agents as active as possible, within a range that ensures the safety of the patient. The dose of a carbonyl stress-ameliorating agent can be adjusted by altering the quantity of an enzyme having glyoxalase I activity immobilized on the carriers, or alternately, the dose of carriers on which the enzyme having glyoxalase I activity has been immobilized.

A carbonyl stress-ameliorating agent of the present invention can be formulated in combination with physiologically acceptable carriers, excipients, diluents, etc., to be administered parenterally as a pharmaceutical composition. Dosage forms for parenteral drug include injections, drops, and so on. The term "injection" encompasses subcutaneous injection, intramuscular injection, intraperitoneal injection, etc.

An injection can be prepared by dissolving a carbonyl compound-reducing agent and an enzyme having glyoxalase I activity as the main ingredients together with an appropriate dispersant, dissolving or dispersing the agent and enzyme in a dispersion medium. Depending on the type of dispersion medium selected, the dosage form can be an aqueous solution or an oleaginous solution. Dispersion media used to prepare aqueous solutions includes distilled water, physiological saline, Ringer solutions, and so on. Various vegetable oils, propyleneglycol, and the like can be used as the dispersion media for preparing an oleaginous solution. Additionally, preservatives, such as paraben, can also be added as needed. In addition, known isotonizing agents, such as sodium chloride, and glucose can be added to the injection. Furthermore, soothing agents, such as benzalkonium chloride or procaine hydrochloride can be added to the injection.

The dose of a carbonyl stress-ameliorating agent of the present invention is selected depending on the type of administration method (dosage form), and condition of subjects (weight, age, sex, symptom, etc.). Generally, in the case of oral administration, a dose of typically 0.001 to 10 mg, more preferably 0.01 to 1 mg/day/kg body weight (human adult) is administered to gain a carbonyl stress-ameliorating effect. The frequency of administration can be selected properly, for example, from a range of 1 to 5 times a day.

The effect of a carbonyl stress-ameliorating agent of the present invention can be confirmed by monitoring the concentration of carbonyl compounds or AGE in blood. The in vivo effect can be assessed by comparing blood AGE levels between a control group and a group wherein a carbonyl stress-ameliorating agent of the present invention has been administered. The control group may be an untreated group or a group wherein physiological saline or a control agent (consisting of the ameliorating agent without the main ingredient, i.e., carbonyl stress-ameliorating agent) has been administered. Glyoxal (GO), methylglyoxal (MGO), 3-deoxyglucosone (3DG), and the like can be used as indices of carbonyl compounds. The levels of these carbonyl compounds can be readily determined by HPLC or the like as shown in the Examples (Ohmori S. et al. J. Chromatogr. 414:149–155, 1987; Yamada H., J. Biol. Chem. 269:20275–20280, 1994). Alternatively, the levels of the carbonyl compounds can be determined by reacting them with 2,4-dinitrophenylhydrazine (2,4-DNPH) under an acidic condition, and measuring the optical density of colored products of the reaction at 360 nm. Further, pentosidine or the like can be used as an index of AGE. A method for quantifying pentosidine with reverse-phase HPLC is already known in the art(Miyata T, et al. J Am Soc Nephrol 7: 1198–1206, 1996). The concentration of carbonyl compounds and AGE in blood or dialysate is detected to assess the effect of a carbonyl stress-ameliorating agent of the present invention outside the living body.

BEST MODE FOR CARRYING OUT THE INVENTION

The present invention is illustrated in detail below with reference to Examples.

Example 1

Methylglyoxal-trapping Effect of Glutathione in Methylglyoxal Solutions (1) Experimental Procedures Methylglyoxal-containing PBS(-) solution and glutathione-containing PBS(-) solution (pH7.4) were combined to prepare solutions containing 400 µM methylglyoxal and 0, 1, 2, 4, or 8 mM glutathione. The solutions were incubated at 37° C. Samples were taken after 0, 2, 4, 8, and 24 hours; and 40 µl of 2 M perchlorate, 40 µl of 1% o-phenylenediamine, and 100 µl of 200 µM glyoxal were added to 100 µl of each sample. The mixtures were stirred, and then incubated at 25° C. for one hour. Quinoxaline derivative, which was produced by the reaction of methylglyoxal and o-phenylenediamine, was separated and quantified by HPLC using reverse-phase column according to the method of Ohmori et al. (Ohmori, S. et al., J. Chromatogr. 414: 149–155, 1987).

(2) Experimental Results

Figure 1:
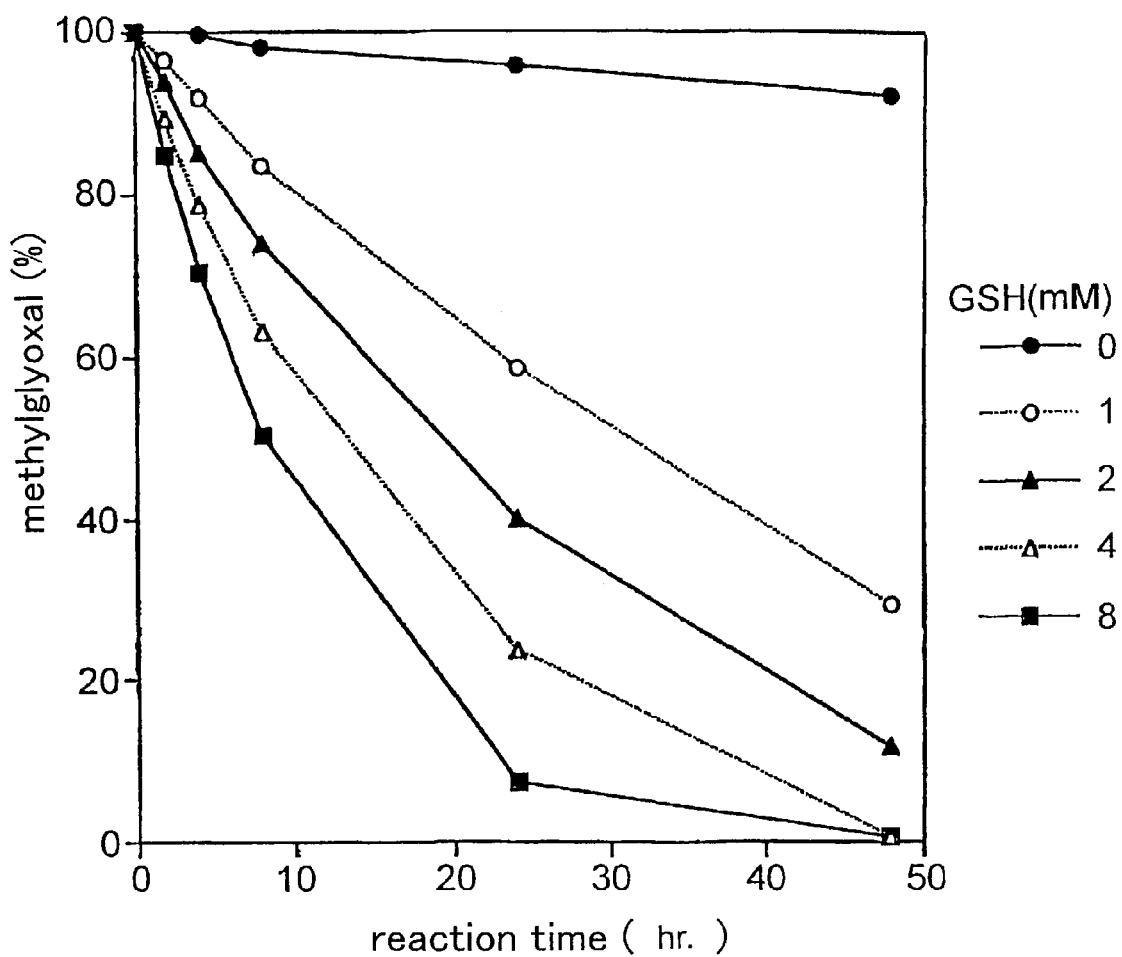
FIG. 1 depicts a graph demonstrating the methylglyoxal-trapping effect of glutathione. The abscissa indicates the reaction time (hr.); the ordinate indicates the residual rate (%) of methylglyoxal taking the amount prior to the reaction (0 hour) as 100%.

Methylglyoxal was trapped by glutathione depending on the concentration of glutathione and incubation time at 37° C. (FIG. 1).

EXAMPLE 2

Elimination of Methylglyoxal from Methylglyoxal Solutions in the Presence of Glutathione and Glyoxal I (1) Experimental Procedures PBS(-) solutions were prepared, whose methylglyoxal concentration were 400 µM, glutathione concentration 4 mM, and the concentration of an enzyme having glyoxalase I activity were 8, 16, 40, and 80 unit/ml, respectively. The solutions were incubated at 37° C. A commercially available enzyme (Sigma) derived from yeast was used as the glyoxalase I. Samples were taken after 1 hour, and then methylglyoxal was quantified by the same method as in Example 1.

(2) Experimental Results

Figure 2:
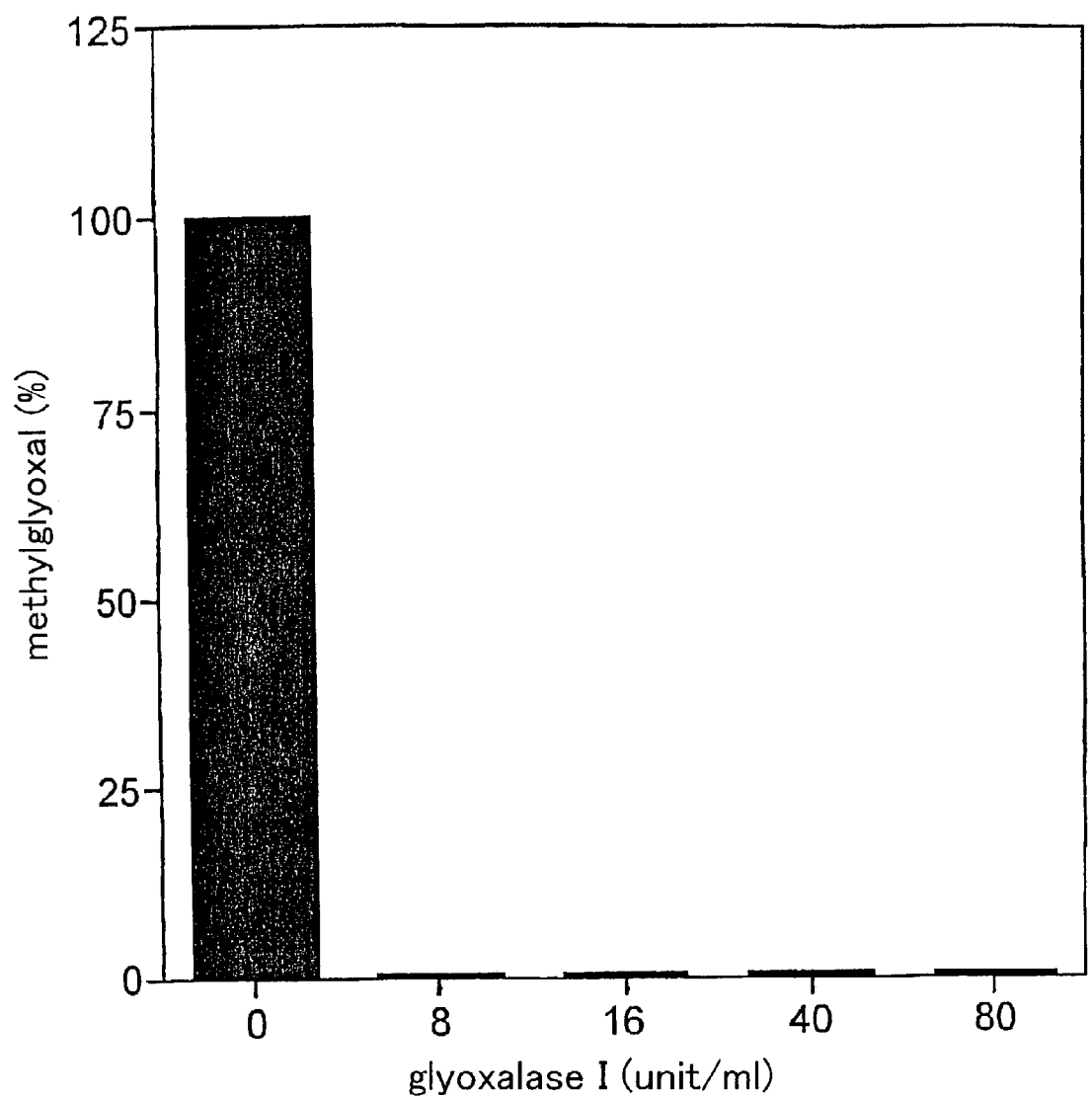
FIG. 2 depicts a graph demonstrating the methylglyoxal-eliminating effect of glyoxalase I addition. The abscissa indicates the concentration of glyoxalase I (unit/ml); the ordinate indicates the residual rate (%) of methylglyoxal taking the amount in the absence of glyoxalase I as 100%.

Approximately 99% of methylglyoxal was eliminated by the addition of glyoxalase I (FIG. 2). The methylglyoxal elimination was demonstrated to be accelerated by the addition of glyoxalase I.

EXAMPLE 3

Elimination of Dicarbonyl Compounds From CAPD Solutions in the Presence of Glutathione and Glyoxalase I (1) Experimental Procedures Glutathione and glyoxalase I (the same as in Example 2) were added to CAPD solution (Baxter Ltd.; PD-4, 1.5) to prepare solutions containing 0, 1, or 4 mM glutathione and 0, 1.3, or 5.2 unit/ml glyoxalase I. The solutions were incubated at 37° C. Samples were taken after 1 hour; 40 µl of 2M perchlorate, 40 µl of 1% o-phenylenediamine, and 100 µl of 20 µM 2,3-butanedione were added to a 100-µl aliquot of each sample. The mixtures were stirred, and then incubated at 25° C. for one hour. Quinoxaline derivative, which were produced by the reaction between o-phenylenediamine, and 3-deoxyglucosone, glyoxal, or methylglyoxal were separated and quantified by HPLC using reverse-phase column according to the method of Ohmori et al. (Ohmori, S. et al., J. Chromatogr. 414: 149–155, 1987).

(2) Experimental Results

Figure 3:
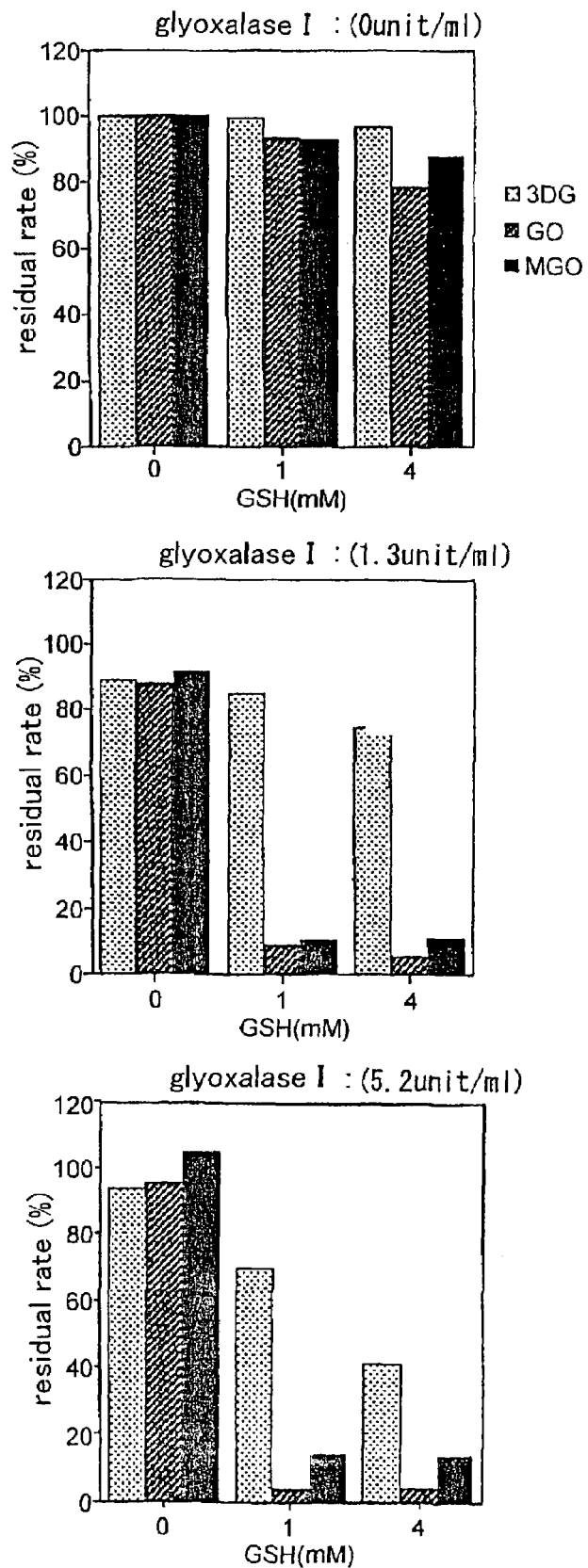
FIG. 3 depicts graphs demonstrating the dicarbonyl compound-eliminating effect of glyoxalase I addition.

By the addition of glyoxalase I and glutathione, dicarbonyl compounds, such as 3-deoxyglucosone, glyoxal, and methylglyoxal, were eliminated from the CAPD solutions (FIG. 3). Thus, dicarbonyl compounds can be effectively removed from CAPD solutions by adding glyoxalase I and glutathione.

EXAMPLE 4

Dicarbonyl Compound-trapping Effect of Glutathione in Mixed Solutions Containing Dicarbonyl Compounds (1) Experimental Procedures PBS(-) solutions (pH7. 4) were prepared, whose concentrations of glyoxal, methylglyoxal, and 3-deoxyglucosone were all 200 µM, glutathione concentration were 0, 0.5, 1, or 5 mM, and glyoxalase I concentration were 0, 0.05, 0.1, 0.5, 1, or 2 unit/ml. The solutions were incubated at 37° C. for 1 hour. 40 µl of 2M perchlorate, 40 µl of 1% o-phenylenediamine, and 100 µl of 50 µM 2,3-butanedione as an internal standard were added to a 100-µl aliquot of each sample; the mixtures were stirred and incubated at 25° C. for 1 hour. Quinoxaline derivative, which was produced by the reaction between o-phenylenediamine and glyoxal, was separated and quantified by HPLC using reverse-phase column according to the method of Ohmori et al. (Ohmori, S. et al., J. Chromatogr. 414:149–155, 1987).

(2) Experimental Results

Figure 4:
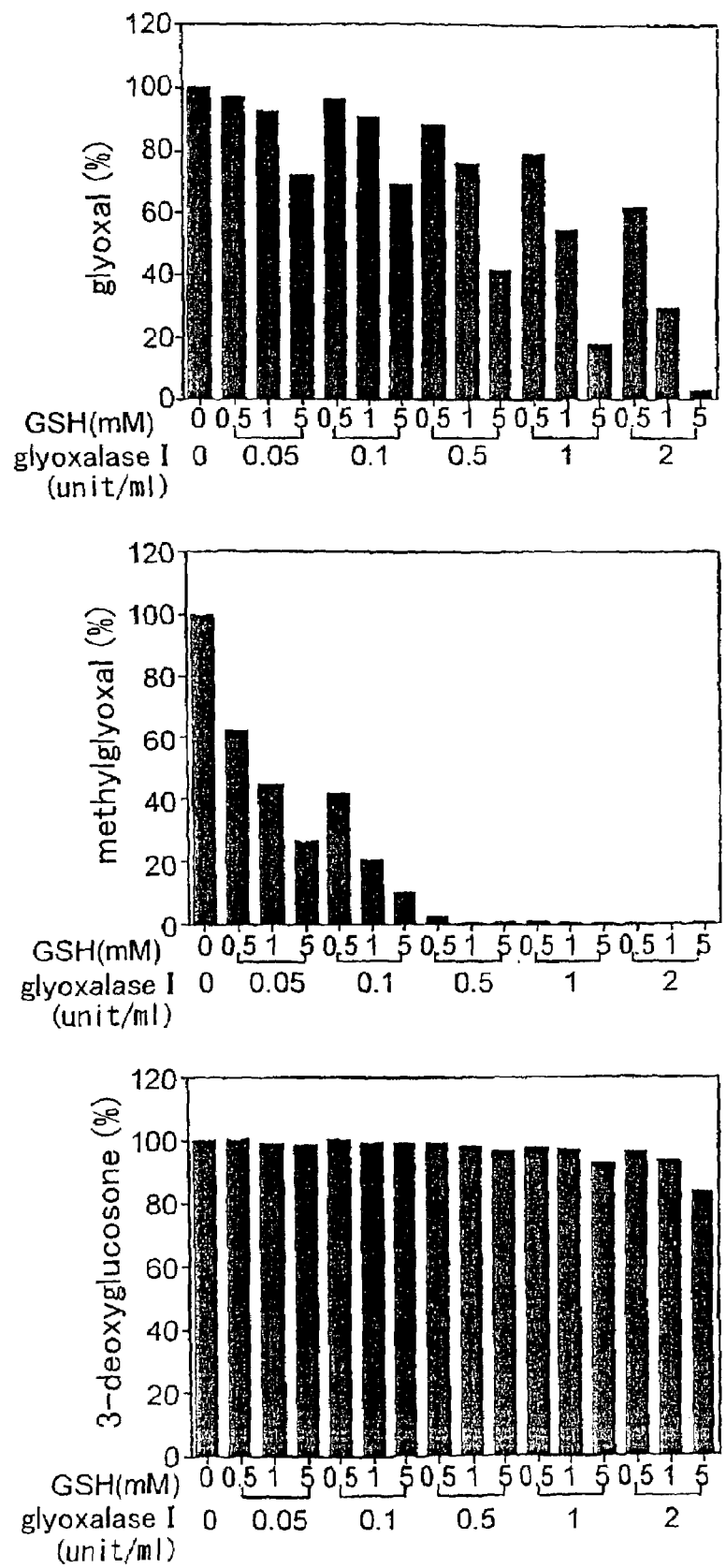
FIG. 4 depicts graphs demonstrating the dicarbonyl compound-trapping effect of glutathione in a mixed solution of three dicarbonyl compounds. The top panel, glyoxal; middle panel, methylglyoxal; bottom panel, 3-deoxyglucosone.

Decrease in the concentrations of dicarbonyl compounds was observed by the addition of glyoxalase I to a mixed solution of dicarbonyl compounds (i.e. glyoxal, methylglyoxal, and 3-deoxyglucosone), and to a solution containing glutathione. Further, as the concentrations of glutathione and glyoxalase I increased, the rate of dicarbonyl compound elimination increased (FIG. 4). In the mixed solution of the three dicarbonyl compounds, the elimination of the less reactive dicarbonyl compound, 3-deoxyglucosone, decreased. This may result from the coexistence of methylglyoxal, which is a highly reactive dicarbonyl compound. Thus, similar experiments were conducted using solutions separately containing each dicarbonyl compound.

EXAMPLE 5

Dicarbonyl Compound-trapping Effect of Glutathione in Solutions Separately Containing Each Dicarbonyl Compound (1) Experimental Procedures PBS(-) solutions (pH 7.4) were prepared, whose glyoxal concentration were 100 μM, glutathione concentration 0, 0.1, 1, or 10 mM, and glyoxalase I concentration 0, 0.01, 0.1, 1, or 10 unit/ml. The solutions were incubated at 37° C. for 1 hour. 40 μl of 2M perchlorate, 40 μl of 1% o-phenylenediamine, and 100 μl of 50 μM 2,3-butanedione as an internal standard were added to a 100-μl aliquot of each sample; the mixtures were stirred and incubated at 25° C. for 1 hour. Quinoxaline derivative, which was produced by the reaction between o-phenylenediamine and glyoxal, was separated and quantified by HPLC using reverse-phase column according to the method of Ohmori et al. (Ohmori, S. et al. , J. Chromatogr. 414:149–155, 1987). The same method was used for methylglyoxal and 3-deoxyglucosone in place of glyoxal.

(2) Experimental Results

Figure 5:
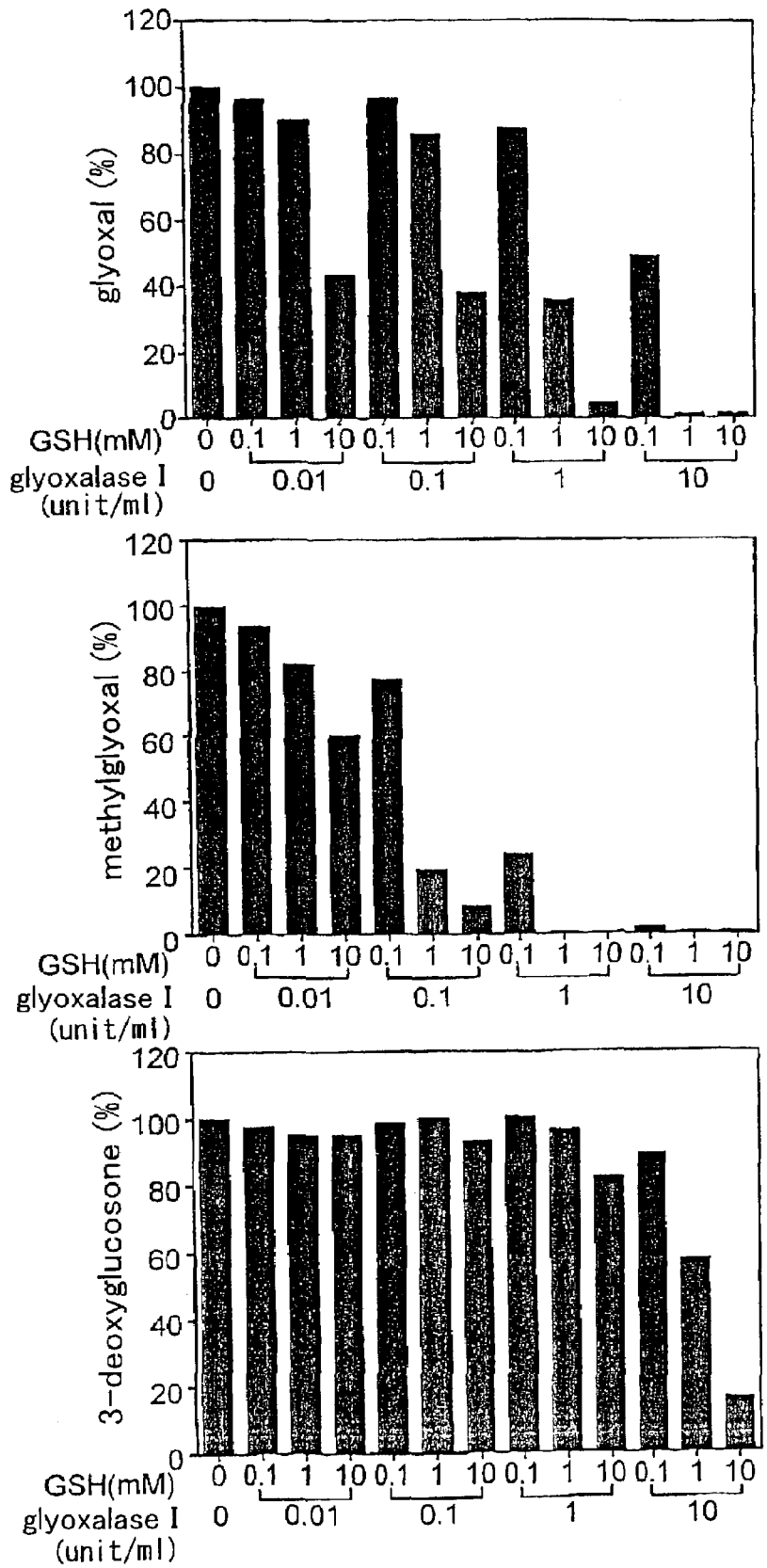
FIG. 5 depicts graphs demonstrating the dicarbonyl compound-trapping effect of glutathione in a solution containing one of the three dicarbonyl compounds. The top panel, glyoxal; middle panel, methylglyoxal; bottom panel, 3-deoxyglucosone.

The concentrations of dicarbonyl compounds decreased with the addition of glyoxalase I to solutions containing glyoxal, methylglyoxal, or 3-deoxyglucosone, and to solutions containing glutathione. Furthermore, depending on the increase of glutathione and glyoxalase I concentrations, the rate of dicarbonyl compound elimination increased (FIG. 5). The elimination of each carbonyl compound was more rapid when the respective compounds were incubated alone than when combined in the reaction solution. Therefore, it was presumed that the most reactive carbonyl compound (i.e., the most toxic), methylglyoxal, is eliminated at first, and then other compounds of the three carbonyl compounds that are less reactive than methylglyoxal are eliminated in sequence from the mixed solution.

EXAMPLE 6

Dilcarbonyl Compound-trapping Effect of Glutathione in CAPD Effluents (1) Experimental Procedures Glutathione and glyoxalase I were added to CAPD effluents (PD-4, 1.5 from Baxter Ltd.; dwelling time, 1 hour, in peritoneal cavity) collected from peritoneal dialysis patients with admission to prepared solutions containing glutathione at a concentration of 5 mM, and glyoxalase I at a concentration of 0, 5, 10, or 20 unit/ml. The solutions were incubated at 37° C. for 1 hour. Samples were taken after 1 hour. 40 μl of 2M perchlorate, 40 μl of 1% o-phenylenediamine, and 100 μl of 20 μM 2,3-butanedione as an internal standard were added to a 100-μl aliquot of each sample; the mixtures were stirred and incubated at 25° C. for 1 hour. Quinoxaline derivative, which were produced by the reaction between o-phenylenediamine, and 3-deoxyglucosone, glyoxal or methylglyoxal, were separated and quantified by HPLC using reverse-phase column according to the method of Ohmori et al. (Ohmori, S. et al., J. Chromatogr. 414: 149–155, 1987).

(2) Experimental Results

Figure 6:
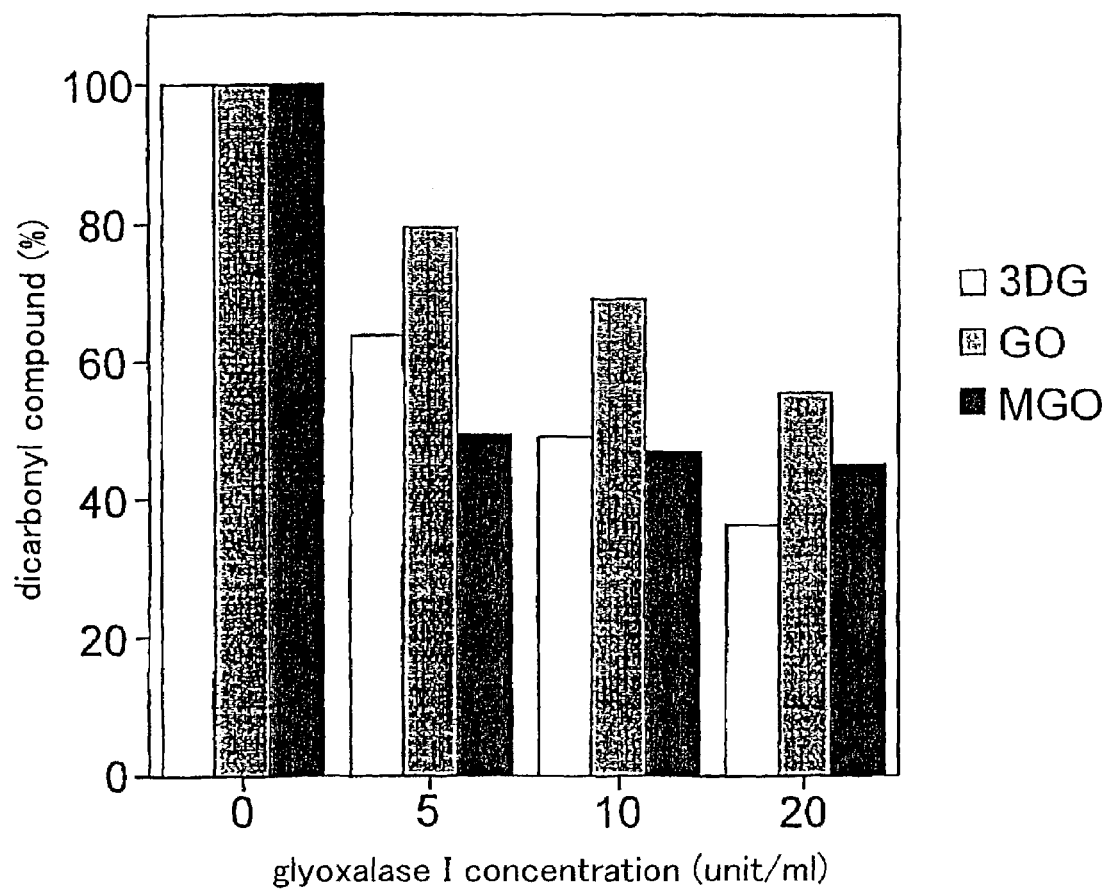
FIG. 6 depicts a graph demonstrating the dicarbonyl compound-eliminating effect of glyoxalase I added in a mixed solution of three dicarbonyl compounds. The abscissa indicates the concentration of glyoxalase I (unit/ml); the ordinate indicates the residual rate (%) of the dicarbonyl compound taking the amount in the absence of glyoxalase I as 100%.

The concentrations of dicarbonyl compounds, such as 3-deoxyglucosone, glyoxal, and methylglyoxal, decreased after the addition of glyoxalase I and glutathione to the CAPD effluents (FIG. 6). Therefore, it was confirmed that dicarbonyl compounds can be eliminated from intraperitoneal CAPD solutions in CAPD patients by adding glyoxalase I and glutathione.

INDUSTRIAL APPLICABILITY

According to the present invention, rapid elimination of carbonyl compounds can be achieved by a carbonyl stress-ameliorating agent of the present invention. The agents are not only effective in eliminating methylglyoxal but are also effective on other major carbonyl compounds, including, 3-deoxyglucosone and glyoxal. Specifically, the significance of the present invention is that the possibility to rapidly eliminate major carbonyl compounds causing carbonyl stress to living bodies was confirmed and which enabled its application as carbonyl stress-ameliorating agents. Since the carbonyl stress-ameliorating agents of the present invention use a reaction of enzymes originally functioning in vivo, they are expected to be highly safe even if delivered via a CAPD solution and such directly into living bodies.

Furthermore, the high specificity due to the use of enzyme reactions is an additional feature of the present invention. Known carbonyl stress-ameliorating agents were previously based on the chemical reactions of compounds. Therefore, their specificities were low and they reacted with all types of carbonyl compounds. Hence, these known agents were predicted to trap not only sugar-derived or lipid-derived carbonyl compounds which are deleterious to living bodies, but also carbonyl groups, such as, pyridoxal that are essential for living bodies. The present invention utilizes enzyme reactions, which are expected to be highly specific for only carbonyl compounds that are deleterious to living bodies.

Furthermore, as confirmed in the above Examples, a carbonyl stress-ameliorating agent of the present invention preferentially eliminates carbonyl compounds with higher reactivities. Specifically, under the coexistence of methylglyoxal, 3-deoxyglucosone, and glyoxal, first, methylglyoxal which greatly affects living bodies is eliminated, and then the other compounds are eliminated. Thus, the carbonyl stress-ameliorating agents of the present invention are excellent not only in the elimination rate of carbonyl compounds but also reacting in a rational way for ameliorating carbonyl-stress state.

The invention claimed is:

1. A method for detoxifying 3-deoxyglucosone in blood or a peritoneal dialysate, comprising the step of contacting said blood or peritoneal dialysate with a purified enzyme having an activity of at least 10 units/ml of glyoxalase I activity in the presence of a carbonyl compound reducing agent in a concentration of at least 1 mM, wherein said 3-deoxyglucosone in said blood or peritoneal dialysate is enzymatically detoxified.

2. The method of claim 1, wherein the method further comprises the step of contacting the blood or peritoneal dialysate with an enzyme having glyoxalase II activity.

3. The method of claim 1, wherein said recombinant enzyme does not comprise glyoxalase II.

4. The method of claim 1, wherein the carbonyl compound-reducing agent is a reduced glutathione or a derivative thereof.

5. The method of claim 4, wherein the reduced glutathione is present at a concentration of 0.1 to 50 mM.

6. The method of claim 1, wherein the enzyme having glyoxalase I activity is immobilized on a carrier.

7. The method of claim 1, wherein glyoxal or methyglyoxal in said blood or dialysate is enzymatically detoxified.

* * * * *

UNITED STATES PATENT AND TRADEMARK OFFICE
CERTIFICATE OF CORRECTION

PATENT NO. : 7,029,906 B2  Page 1 of 1
APPLICATION NO. : 10/168695
DATED : April 18, 2006
INVENTOR(S) : Miyata et al.

It is certified that error appears in the above-identified patent and that said Letters Patent is hereby corrected as shown below:

On the title page, item [73]:
Assignee information change the words "TOKAI UNIVERSITY EDUCATION SYSTEM" to --TOKAI UNIVERSITY EDUCATIONAL SYSTEM --.

Signed and Sealed this

Twenty-fifth Day of July, 2006

JON W. DUDAS
*Director of the United States Patent and Trademark Office*